(12) United States Patent
Ramanathan et al.

(10) Patent No.: US 9,808,593 B1
(45) Date of Patent: Nov. 7, 2017

(54) APPARATUS FOR ENHANCEMENT OF OXYGEN AND/OR AIR FLOW CONTROL TO NASAL PRONGS

(75) Inventors: Rangasamy Ramanathan, La Canada, CA (US); Arnold M. Heyman, Los Angeles, CA (US); Thomas R. Thornbury, Los Angeles, CA (US); Craig R. McCrary, Los Angeles, CA (US)

(73) Assignee: Neotech Products LLC, Valencia, CA (US)

( * ) Notice: Subject to any disclaimer, the term of this patent is extended or adjusted under 35 U.S.C. 154(b) by 488 days.

(21) Appl. No.: 13/385,149

(22) Filed: Feb. 6, 2012

(51) Int. Cl.
| | |
|---|---|
| *A61M 15/08* | (2006.01) |
| *A62B 7/00* | (2006.01) |
| *A61M 16/06* | (2006.01) |
| *A61M 16/08* | (2006.01) |

(52) U.S. Cl.
CPC .... *A61M 16/0672* (2014.02); *A61M 16/0816* (2013.01)

(58) Field of Classification Search
CPC .......... A61M 16/0816; A61M 16/0672; A61M 16/0666

USPC ........... 128/200.24, 204.18, 204.24, 204.25, 128/206.11, 207.18, 912
See application file for complete search history.

(56) References Cited

U.S. PATENT DOCUMENTS

| | | | | |
|---|---|---|---|---|
| 4,818,320 | A  * | 4/1989 | Weichselbaum | 156/227 |
| 5,074,299 | A  * | 12/1991 | Dietz | 128/204.21 |
| 6,863,069 | B2 * | 3/2005 | Wood | 128/207.18 |
| 2002/0112730 | A1* | 8/2002 | Dutkiewicz | 128/207.18 |
| 2005/0066976 | A1* | 3/2005 | Wondka | 128/207.18 |
| 2008/0121230 | A1* | 5/2008 | Cortez et al. | 128/204.17 |
| 2008/0216838 | A1* | 9/2008 | Wondka | 128/205.25 |
| 2011/0125052 | A1* | 5/2011 | Davenport et al. | 600/561 |
| 2011/0253136 | A1* | 10/2011 | Sweeney et al. | 128/203.12 |

FOREIGN PATENT DOCUMENTS

WO   WO2009/146484   * 12/2009

* cited by examiner

*Primary Examiner* — Kristen Matter
(74) *Attorney, Agent, or Firm* — Kelly & Kelley, LLP

(57) ABSTRACT

Nasal cannula apparatus, includes in an inlet tubular fitting sized and configured to directly endwise connect to a source of oxygen, or oxygen and air. The fitting defines an inlet flow passage area A, having a 15 mm external diameter. A pair of tubular prongs is operatively connected with the inlet fitting, and receivable in an infant's nostrils to deliver oxygen, or oxygen and air flow to the infant, the prongs each having flow passing area $A_3$, and $A_1 \gg A_3$.

5 Claims, 4 Drawing Sheets

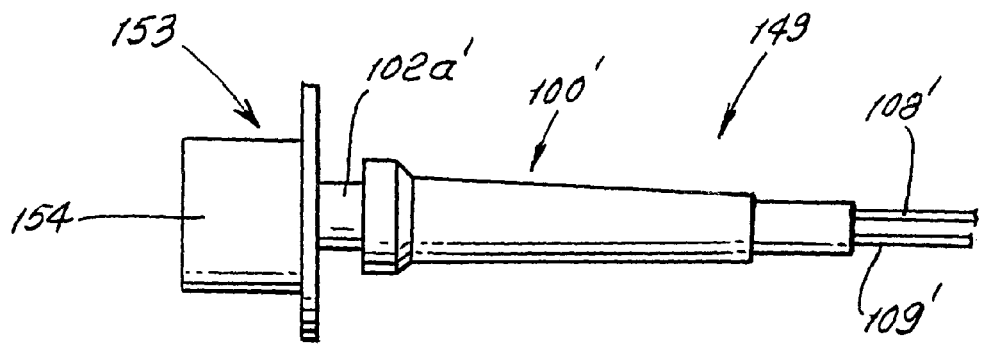
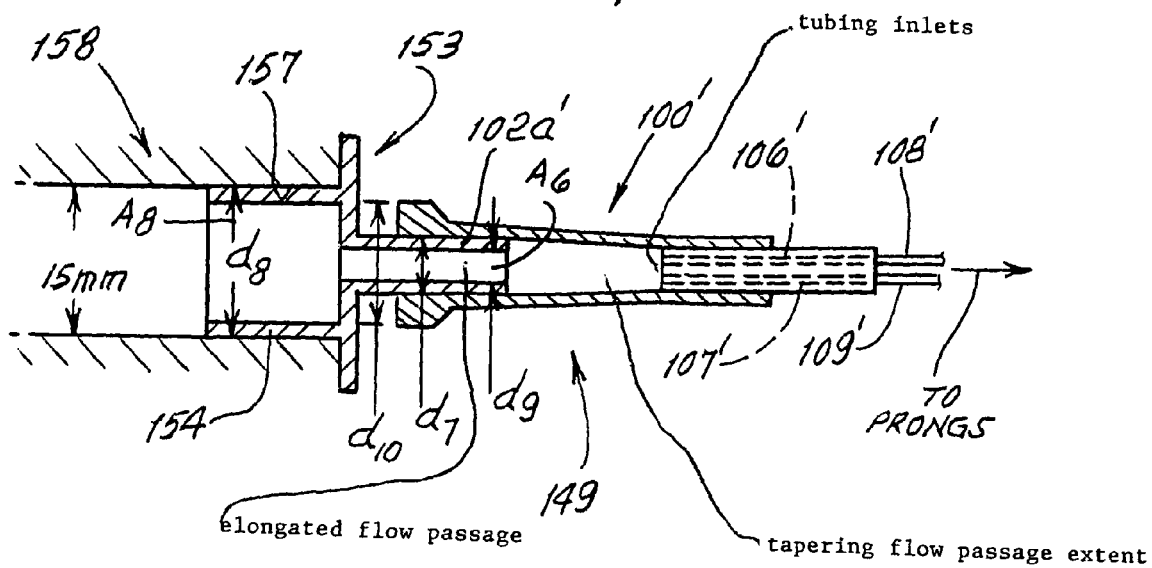

APPARATUS FOR ENHANCEMENT OF OXYGEN AND/OR AIR FLOW CONTROL TO NASAL PRONGS

BACKGROUND OF THE INVENTION

This invention relates generally to nasal cannula therapy, and more particularly to improvements concerning tubing flow in nasal cannula therapy systems.

An accepted modality for respiratory support of the newborn is via a mechanical ventilator. The interface is usually an endotracheal tube which is passed via the mouth or nose, across the oropharynx, through the trachea and placed in the main stem bronchus. This placement, although physiologically effective, has many side effects such as irritation, trauma, infection, increased work of breathing and even bronchopulmonary dysplasia. In order to overcome the sequelae or shortcomings, a device is needed to deliver via the mechanical ventilator the needed pressures to support the newborn. The ventilator is necessary to support the breathing of those that cannot breath spontaneously on their own either because of prematurity of the breathing mechanism or other congenital pathological conditions which cannot maintain the oxygenation of the patent. Once the patient is able to breath spontaneously, the cannula can be adapted to less invasive modalities which include continuous, positive, airway pressure (CPAP), Bubble CPAP, High Flow or simple oxygen therapy.

There is need for a device that can be adapted to all of the above methods by applying specifically designated adapters. This increases the utility of the device.

Thus, the needed cannula can be used from the delivery room all the way to patient discharge and meet all the respiratory needs of the newborn.

SUMMARY OF THE INVENTION

It is a major object of the invention to provide solutions to the above problems and difficulties, and to provide a simple, reliable, adjustable connection or connections between air supply means and nasal cannula tubing, and particularly to provide means enabling assisted intermittent positive pressure in a non-invasive mode.

SUMMARY OF THE INVENTION

It is a further major object of the invention to provide an improved nasal cannula apparatus that comprises:

a) an inlet tubular fitting sized and configured to directly endwise connect to a source of oxygen, or oxygen and air, said fitting defining an inlet flow passage area A, having a 15 mm external diameter, b) a pair of tubular prongs operatively connected with the inlet fitting, and receivable in an infant's nostrils to deliver oxygen, or oxygen and air flow to the infant, the prongs each having flow passing area $A_3$, c) and wherein $A_1 \gg A_3$.

As will be seen, all flow passages between $A_1$ and $A_3$ have flow passing cross sectional areas greater than $A_3$. Also $A_3$, the flow passing area of each prong, has a diameter greater than 1.0 mm, and may preferably be about 2.5 mm.

Another object is to provide an inlet fitting having two outlets respectively connected in series with two flexible tubes leading to the two prongs, those tubes typically being of equal length and there being ribbing in the tubes to resist their kinking.

A further object is to provide two nasal prongs that fit in an infant's nostrils, and that have matching curvature along the prong lengths, to match normal curvature of nasal canal.

Yet another object is to provide an adapter as for example may be selected from a set of adaptors, to enable ready connection of a nasal cannula inlet fitting to a source of $O_2$, or air and $O_2$.

DRAWING DESCRIPTION

FIG. 6 shows use of an intermediate adapter; and

FIG. 7 is an axial section taken through FIG. 6.

DETAILED DESCRIPTION

Figure 1:
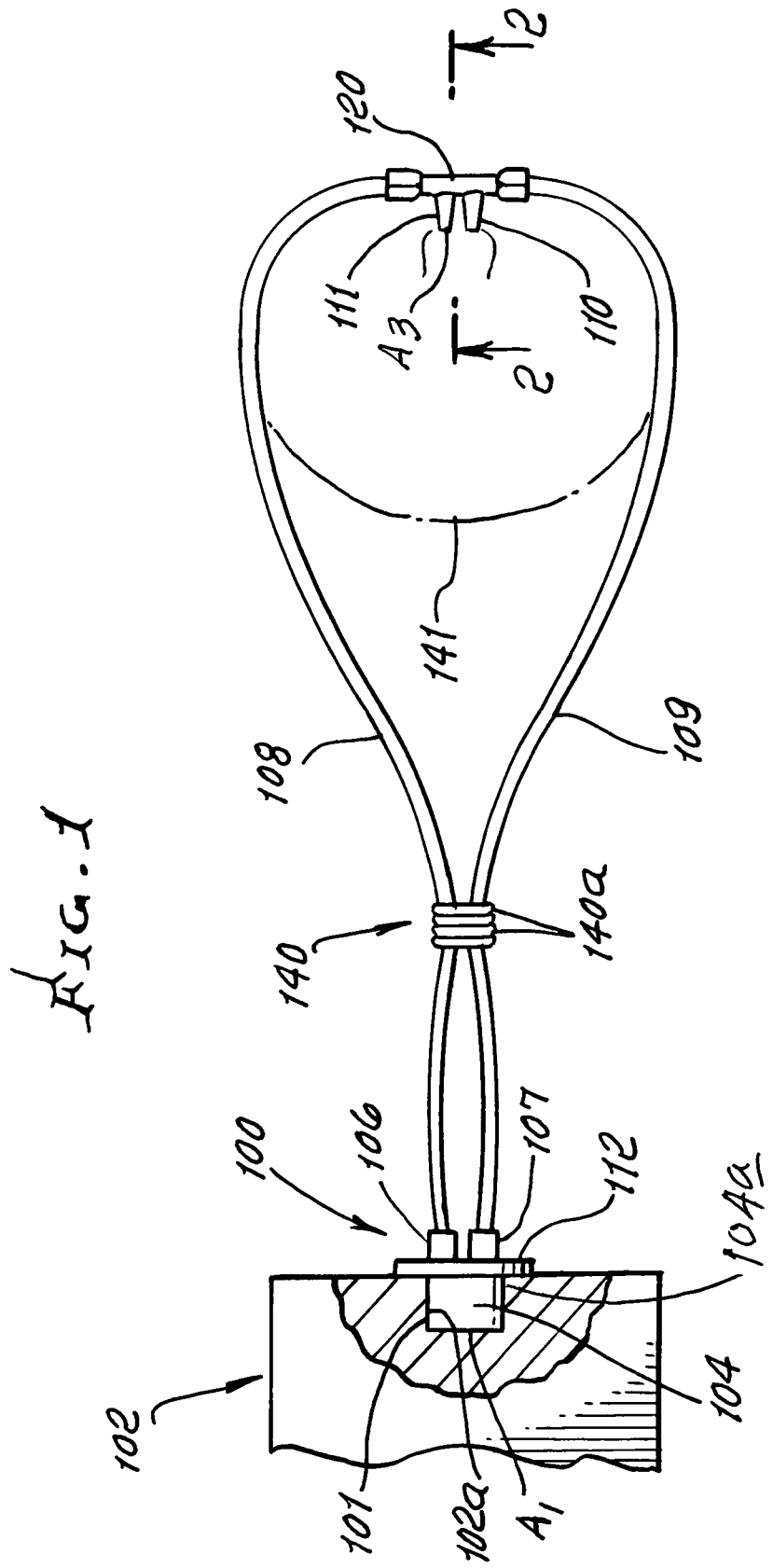
FIG. 1 is a view of apparatus incorporating the invention.

Referring first to FIG. 1, a basic form of the invention provides a rigid plastic tubular fitting 100 sized and configured to directly endwise connect at 101 with an oxygen supply ventilator or other oxygen, or oxygen and air, source, 102, as via bore 102a. The bore 102a is typically a 15 mm ID bore, with ability to connect to other devices and systems.

Figure 4:
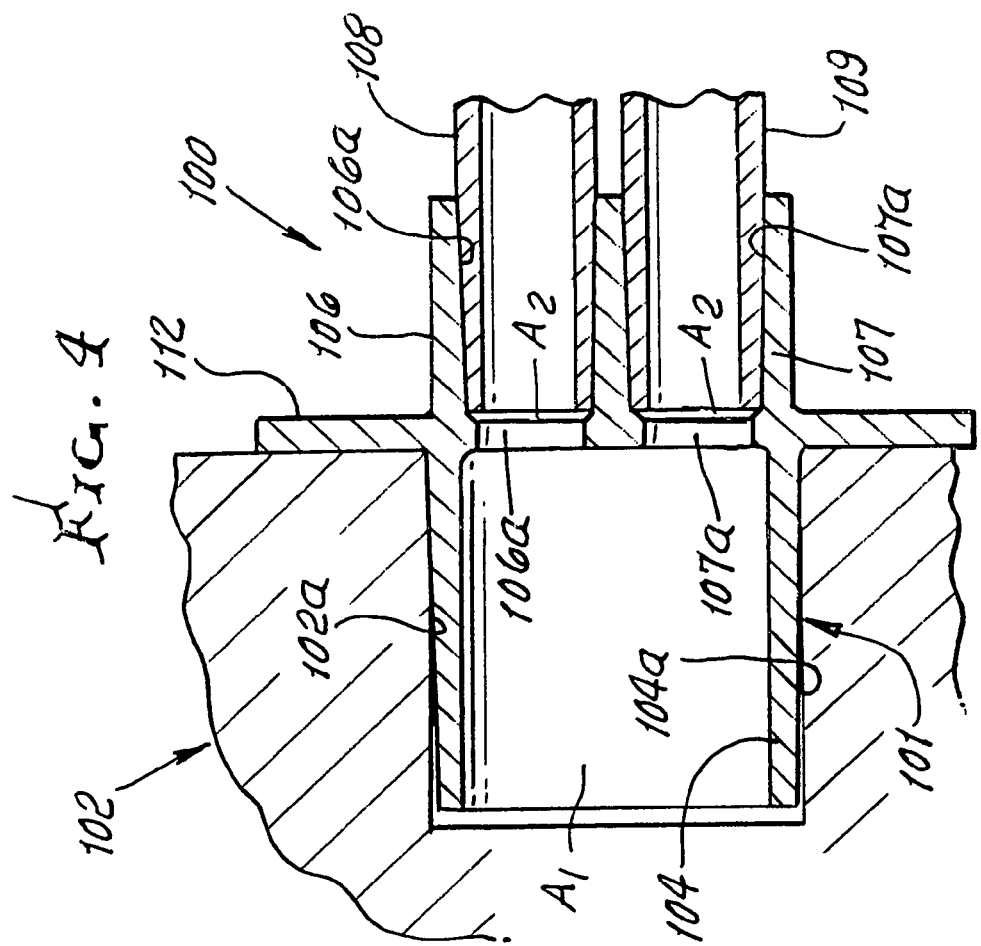
FIG. 4 is an axial section taken through a fitting connectable to a ventilator.
Figure 5:
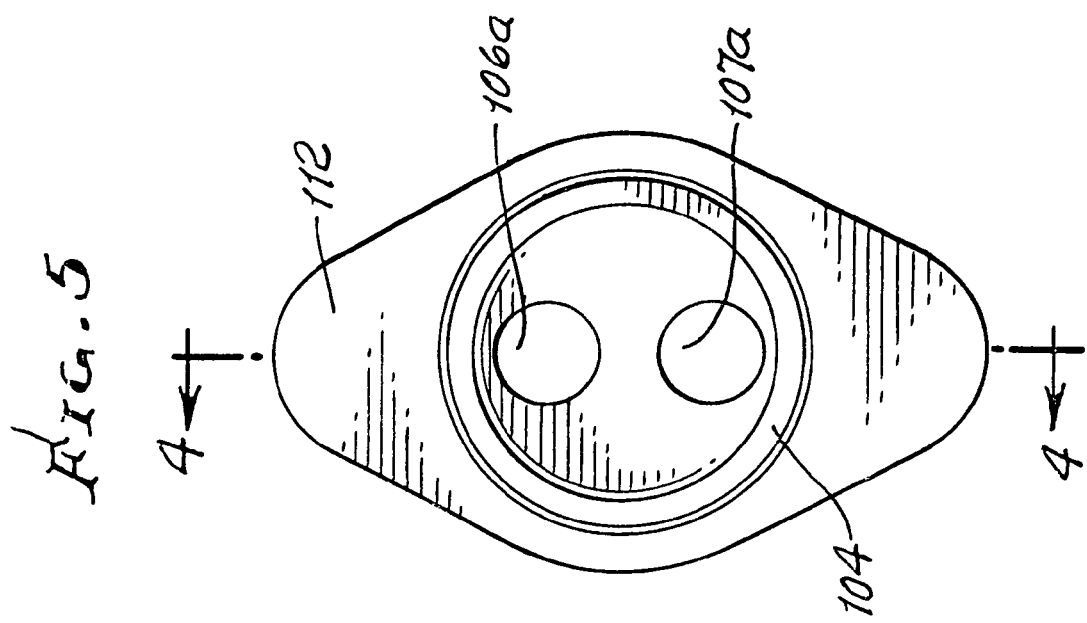
FIG. 5 is an end view of the FIG. 4 fitting.

Referring also to FIG. 4, the fitting 100 has a flow inlet tubular stem 104 insertible into the bore 102a of a ventilator circuit or device 102 that supplies oxygen or mixed air and oxygen. The outer surface 104a of stem 104 may be configured, for interference fit, and frictional retention. The fitting has two flow outlets 106a and 107a, extending in parallel relation, and aligned with two tubular stems 106 and 107. Cannula tubings or ducts 108 and 109 are insertible into stems 106 and 107 for frictional retention, and stem bores 106a and 107a are sized to retain the typically plastic tubings 108 and 109, which extend to nasal tubular prongs 110 and 111, as seen in FIG. 1. A rigid plastic flange 112 merges with the two stems 106 and 107, for finger manipulation of the fitting.

Figure 2:
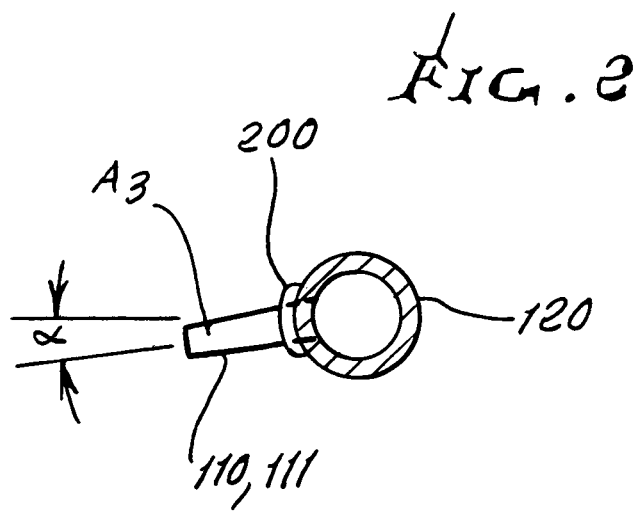
FIG. 2 is a section taken on lines 2-2 of FIG. 1, the view of nasal prongs showing lengthwise angularity or curvature.

Nasal cannula plastic tubing is connected in series with the fitting 100, and typically include like flexible tubular branches 108 and 109 connected to stems 106 and 107, and leading to opposite ends of short length tubing connection 120 from which the two nasal prongs 110 and 111 extend sidewardly. See also FIG. 2. The prongs 110 and 111 have slight endwise deflection or curvature, to match anatomical curvature of nasal canal. See deviation angles α which are between 2° and 10°. A soft sealing cushion 200 may be employed adjacent the bases of the prongs, to abate leakage of air or $O_2$ delivered to the prong outlets, and to enhance comfort.

Figure 3:
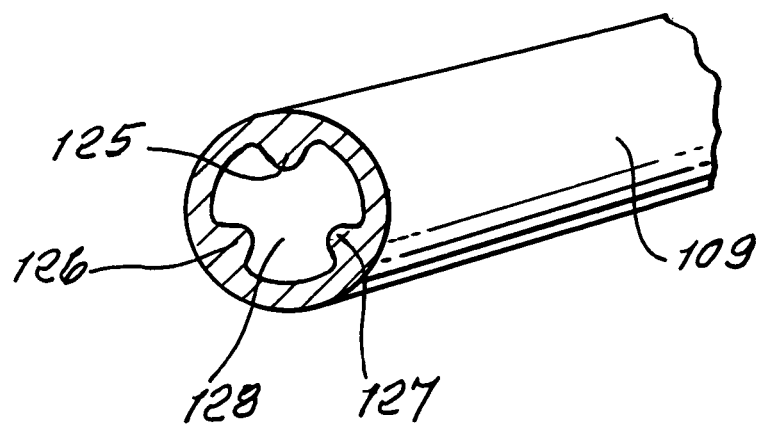
FIG. 3 is a perspective view showing internal ribbing in tubing.

FIG. 3 shows ribbing 125-127 integral with and projecting radially inwardly in flexible plastic duct branch 109 to stiffen it against extreme bending or kinking that would restrict oxygen or air flow in that duct. Open flow space remains at 128, within the duct or branch and between the ribs. Both of the flexible elongated branches 108 and 109 may contain such ribs, which are alike and extend lengthwise within the branches.

In order to secure a cannula around the patient's head 141, the cannula utilizes a securing ring 140 seen in FIG. 1. This cannula O-ring uses a soft, silicone material that has four like annular rings 140a. The soft material will not cause trauma to the head. The rings 140*a* allow the ring 140 to adjustably slide up and down the tubing securely, while providing a frictional grip to the tubing outside surfaces, making it easier to grasp the ring to move it. The securing rings 140*a* are typically also color coded, to differentiate or indicate which size prongs are on the cannula. the cannula tubing itself may have green coloring, to indicate use for oxygen flow.

Additional features of the invention include the following:

i) The ID of the cannula adapter and tubing is larger than the ID opening of the cannula prongs. The prongs at their openings, have the smallest ID of the system. This allows for various oxygen therapy treatments to be effectively delivered through the device. Small bore i.e. less than 1 mm bore size prongs, which restricts flows and limits pressures, is typically not used.

ii) The nasal prongs having a slight curvature, are angled at and near their ends, which allows supplied air to flow precisely into the anatomical curve of the nasal passage. (If a prong rests against cannula wall it may traumatize that wall). The 15 mm adapter allows connection to various respiratory support systems, which in turn allows multiple respiratory support methods to be applied to the infant while in the hospital. The respiratory interface can be used upon the baby at delivery and then remain on the baby while multiple other respiratory support treatments are applied. The 15 mm inlet size allows the device to be used at birth, in labor and delivery, with manual resuscitation bag or automated delivery systems.

iii) With the addition of the unique oxygen adapter, the cannula can connect to oxygen tubing while remaining on the baby, i.e. with prongs in the nose, but also allowing transition from non-invasive mechanical ventilation or non-invasive continuous positive pressure to regular oxygen therapy without changing the $O_2$ delivery interface, as at a ventilator.

iv) The use of a 15 mm "Y" inlet connector or fitting allows connection of oxygen supply to the inspiratory limb and a supply to the inspiratory limb and a pressure relief valve to the expiratory limb.

v) With the addition of the disclosed oxygen adapter, one can utilize high frequency oscillatory ventilation, via cannula.

vi) The cannula tubing with support ribs on the ID, helps prevent the tube or tubing from kinking. The tubing also may have a translucent tint, preferably green for oxygen therapy.

vii) In order to secure a cannula around the patients head, a cannula embracing O-ring consists of a soft silicone material that has at least three ribs or rings spaced lengthwise of the tubing. The soft material will not cause trauma. The ribs allow a securing ring to slide lengthwise up and down the tubing, securely, while providing a grip to the outside surface, making it easier to grasp the ring to move it. The securing rings are also color coded, to indicate which size prongs are on the cannula.

viii) The device provides a utilitarian aspect to the respiratory needs of the newborn to ventilate the lungs. At birth, some newborns do not have the ability to spontaneously breath. Thus there is a need for the assistance of respiration with mechanical respiration. The inspiratory and expiratory phases are supplied by the ventilator. The delivery can be with an invasive endrotracheal tube or via an external cannula. Once the baby can breathe by itself, a constant pressure is applied by an external cannula to keep the lung airsacks open. With continued clinical improvements the applied constant pressure is substituted with a relative high flow of gas and as decreased. When the clinical condition is stabilized, all external assistance is discontinued.

The device described herein satisfies the needs for respiratory support in each step described. Therefore, instead of multiple devices being applied, only one device need be utilized from delivery to patient discharge from the hospital.

FIGS. 6 and 7 show an inlet fitting 100' of nasal cannula device 149 connected at 106' and 107' to cannula tubing 108' and 109' of FIG. 1. corresponding to tubing branches 108 and 109. Fitting 100' has an inlet internal diameter $d_7$ which is not 15 mm, and an external diameter $d_{10}$ which is not 15 mm. An adapter 153 is provided having tubular outlet 102*a*' that fits the inlet internal diameter $d_7$ of fitting 100'. Intermediate adaptor 153 has a tubular inlet with external diameter $d_8$ equal to 15 mm, to be receivable in 15 mm bore 157 of air supply ventilator 158. The area of the ventilator bore is indicated at $A_8$. In this way, the cannula device 149, similar to the FIG. 1 device, can be adapted to the 15 mm outlet of the ventilator. As $O_2$ or air and $O_2$, flows from the ventilator, through the adapter 153, through the fitting 100', through tubing 108' and 109' and to the cannula nasal prongs, it encounters flow passages of decreasing cross-sectional areas.

Accordingly, the following is provided for connection to the 15 mm bore of $O_2$ or air and $O_2$ supply means:

a) a nasal cannula device having an inlet fitting of external diameter $d_{10}$ where $d_{10}$ is not equal to 15 mm, b) an adaptor having an external diameter $d_8$ equal to 15 mm connected to said supply means bore and an outlet bore of diameter $d_9$ connected to said device, c) the flow areas of said adaptor and of said device being less than the flow area $A_8$ of said supply means bore and diminishing in the direction toward nasal prongs defined by said nasal cannula device. See also flow area $A_6$.

We claim:

1. An improvement for a nasal cannula apparatus that includes a pair of tubular prongs receivable in an infant's nostrils to deliver oxygen, or oxygen and air flow to the infant, said prongs each having flow passing area $A_3$, the improvement comprising a) an inlet tubular adaptor sized and configured to directly endwise connect to a source of oxygen, or oxygen and air, said adaptor defining an inlet flow passage area $A_1$ and said adaptor having a 15 mm external diameter, b) said adaptor defining two like outlet flow passages operatively connectible with said nasal cannula apparatus incorporating said prongs, there being two parallel venturi passages intervening between said adaptor inlet flow passage and outlets defined by said adaptor outlet flow passages, said venturi passages having overall width less than a diameter of said inlet flow passage defined by the adaptor, said adaptor outlet flow passages each having area $A_2$, where $A_1 > A_2 > A_3$.

2. The improvement of claim 1 wherein said prongs are elongated and have lengthwise curvature.

3. The improvement of claim 1 including cushion structure through which the prongs extend to cushion against nasal surfaces.

4. The improvement of claim 1 including sealing structure through which the prongs extend.

5. The improvement of claim 1 wherein each said adaptor outlet flow passage has an associated external diameter less than 15 mm.

\* \* \* \* \*